(12) United States Patent
Kalender et al.

(10) Patent No.: US 7,881,427 B2
(45) Date of Patent: Feb. 1, 2011

(54) BREAST LOCATING MEANS WITH SAMPLE CONTAINER FOR AN INSTRUMENT FOR EXAMINING A FEMALE BREAST

(75) Inventors: Willi Kalender, Moehrendorf (DE); Harry Schilling, Eichstaett (DE)

(73) Assignee: MIR Medical Imaging Research Holding GmbH, Moehrendorf (DE)

( * ) Notice: Subject to any disclaimer, the term of this patent is extended or adjusted under 35 U.S.C. 154(b) by 0 days.

(21) Appl. No.: 12/401,814

(22) Filed: Mar. 11, 2009

(65) Prior Publication Data

US 2010/0080346 A1 Apr. 1, 2010

(30) Foreign Application Priority Data

Sep. 29, 2008 (DE) .................. 10 2008 042 430

(51) Int. Cl.
*A61B 6/04* (2006.01)
(52) U.S. Cl. ........................................ 378/37
(58) Field of Classification Search ............. 378/4, 378/19, 37, 62, 20, 208
See application file for complete search history.

(56) References Cited

U.S. PATENT DOCUMENTS

| | | | |
|---|---|---|---|
| 3,673,394 A | 6/1972 | Hartmann |
| 4,015,836 A | 4/1977 | Redington et al. |
| 4,400,827 A | 8/1983 | Spears |
| 4,680,028 A | 7/1987 | Stuart |
| 4,709,382 A | 11/1987 | Sones |
| 5,273,435 A | 12/1993 | Jacobson |
| 5,308,321 A | 5/1994 | Castro |
| 5,386,447 A | 1/1995 | Siczek |
| 5,426,685 A | 6/1995 | Pellegrino et al. |
| 5,528,043 A | 6/1996 | Spivey et al. |
| 5,569,266 A | 10/1996 | Siczek |
| 5,609,827 A | 3/1997 | Russell et al. |

(Continued)

FOREIGN PATENT DOCUMENTS

DE 19639975 5/1998

(Continued)

OTHER PUBLICATIONS

Mun et al., "Active RFID System Augmented with 2D Barcode for Asset Management in a Hospital Setting," IEEE International Conference on RFID, Mar. 2007, pp. 205-211.

(Continued)

*Primary Examiner*—Irakli Kiknadze
(74) *Attorney, Agent, or Firm*—Kevin L. Daffer; Daffer McDaniel, LLP

(57) ABSTRACT

An X-ray machine, which in one embodiment is based on a spiral CT scanner, is used for examining a breast of a female patient. The X-ray machine has a gantry, which is adapted for rotation about a rotational axis, and simultaneously, for movement in a direction parallel to the rotational axis. A cylindrical imaging region is scanned along a spiraling path provided by the gantry. The patient is positioned so that a breast to be examined projects into the imaging region. A sample receptacle located in the imaging region is adapted to accommodate a tissue sample and/or a reference material. A range of movement of the gantry is dimensioned, so that the breast and/or the contents of the sample receptacle can be imaged with the gantry.

11 Claims, 3 Drawing Sheets

U.S. PATENT DOCUMENTS

| | | | |
|---|---|---|---|
| 5,664,569 | A | 9/1997 | Damadian et al. |
| 5,757,878 | A | 5/1998 | Dobbs et al. |
| 5,803,912 | A | 9/1998 | Siczek et al. |
| 6,242,743 | B1 | 6/2001 | DeVito et al. |
| 6,254,614 | B1 | 7/2001 | Jesseph |
| 6,298,114 | B1 | 10/2001 | Yoda |
| 6,325,537 | B1 | 12/2001 | Watanabe |
| 6,358,246 | B1 | 3/2002 | Behl et al. |
| 6,415,012 | B1 | 7/2002 | Taguchi et al. |
| 6,418,188 | B1 | 7/2002 | Broadnax |
| 6,419,390 | B1 | 7/2002 | Landis-Lowell |
| 6,463,122 | B1 | 10/2002 | Moore |
| 6,480,565 | B1 | 11/2002 | Ning |
| 6,684,097 | B1 | 1/2004 | Parel et al. |
| 6,819,736 | B1 | 11/2004 | Bruder et al. |
| 6,837,772 | B1 | 1/2005 | Luk |
| 6,872,001 | B1 * | 3/2005 | Gilevich .................. 378/208 |
| 7,005,988 | B2 | 2/2006 | Mathewson, II et al. |
| 7,065,393 | B2 | 6/2006 | Sati et al. |
| 7,304,578 | B2 | 12/2007 | Sayers et al. |
| 7,453,978 | B1 | 11/2008 | DiBianca et al. |
| 7,467,892 | B2 | 12/2008 | Lang et al. |
| 7,492,858 | B2 | 2/2009 | Partain et al. |
| 7,556,426 | B2 | 7/2009 | Nakajo et al. |
| 7,558,370 | B2 | 7/2009 | Sommer, Jr. et al. |
| 7,677,799 | B2 | 3/2010 | Jensen et al. |
| 7,697,660 | B2 | 4/2010 | Ning |
| 7,743,953 | B2 | 6/2010 | Okazaki et al. |
| 7,764,765 | B2 | 7/2010 | Ohta et al. |
| 2002/0181651 | A1 | 12/2002 | Shepherd et al. |
| 2003/0072409 | A1 | 4/2003 | Kaufhold et al. |
| 2003/0204965 | A1 | 11/2003 | Hennessey |
| 2004/0066880 | A1 | 4/2004 | Oikawa |
| 2004/0082856 | A1 | 4/2004 | Marmarelis |
| 2004/0092826 | A1 | 5/2004 | Corbeil et al. |
| 2004/0238750 | A1 | 12/2004 | Vafi et al. |
| 2004/0251419 | A1 | 12/2004 | Nelson et al. |
| 2004/0254461 | A1 | 12/2004 | Ackerman, III |
| 2005/0070817 | A1 | 3/2005 | Mueller, Jr. |
| 2006/0094950 | A1 | 5/2006 | Ning |
| 2006/0145871 | A1 | 7/2006 | Donati et al. |
| 2006/0262898 | A1 | 11/2006 | Partain et al. |
| 2007/0009080 | A1 | 1/2007 | Mistretta |
| 2007/0064867 | A1 | 3/2007 | Hansen et al. |
| 2007/0092059 | A1 | 4/2007 | Wayne Eberhard et al. |
| 2007/0237306 | A1 | 10/2007 | Jones et al. |
| 2007/0238957 | A1 | 10/2007 | Yared |
| 2008/0033420 | A1 | 2/2008 | Nields et al. |
| 2008/0037703 | A1 | 2/2008 | Ting |
| 2008/0081984 | A1 | 4/2008 | Lafferty |
| 2008/0084961 | A1 * | 4/2008 | Keppel et al. ............ 378/37 |
| 2008/0089471 | A1 | 4/2008 | Kobayashi |
| 2008/0101538 | A1 | 5/2008 | Schliermann |
| 2008/0187095 | A1 * | 8/2008 | Boone et al. .............. 378/37 |
| 2008/0205588 | A1 | 8/2008 | Kim |
| 2008/0221443 | A1 | 9/2008 | Ritchie et al. |
| 2008/0221478 | A1 * | 9/2008 | Ritchie et al. ............ 600/562 |
| 2008/0230074 | A1 | 9/2008 | Zheng et al. |
| 2009/0080604 | A1 * | 3/2009 | Shores et al. ............ 378/37 |
| 2009/0196393 | A1 | 8/2009 | Wang et al. |

FOREIGN PATENT DOCUMENTS

| | | |
|---|---|---|
| DE | 19812995 | 10/1999 |
| DE | 10026792 | 12/2001 |
| DE | 10207623 | 11/2003 |
| DE | 102004042790 | 3/2006 |
| DE | 102005022347 | 11/2006 |
| DE | 102005048049 | 4/2007 |
| EP | 0435837 | 7/1991 |
| EP | 1549115 | 6/2005 |
| EP | 1700568 | 9/2006 |
| EP | 1864611 | 12/2007 |
| JP | 2008272093 | 11/2008 |
| WO | 93/17620 | 9/1993 |
| WO | 94/06352 | 3/1994 |
| WO | 98/49939 | 11/1998 |
| WO | 99/30615 | 6/1999 |
| WO | 2004/006755 | 1/2004 |
| WO | 2004/043535 | 5/2004 |
| WO | 2006/119426 | 11/2006 |
| WO | 2007/120622 | 10/2007 |
| WO | 2008/024611 | 2/2008 |
| WO | 2008/054279 | 5/2008 |

OTHER PUBLICATIONS

Nishide et al., "Micro-focus x-ray CT imaging of breast specimens with microcalcifications," 89th Scientific Assembly and Annual Meeting of the Radiological Society of North America, Dec. 2003, pp. 1662-1663.

Tornai et al., "Design and Development of a Fully-3D Dedicated X-ray Computed Mammotomography System," Proceedings of SPIE, vol. 5745, 2005, pp. 189-197.

Bentzen et al., "Isotherm mapping in hyperthermia using subtraction X-ray computed tomography," Radiotherapy and Oncology, vol. 2, 1984, pp. 255-260.

Griffiths et al., "Applied potential tomography for non-invasive temperature mapping in hyperthermia," Clin. Phys. Physiol. Meas., vol. 8, Suppl. A, 1987, pp. 147-153.

Jenne et al, "CT On-Line Monitoring of HIFU Therapy," IEEE Ultrasonics Symposium, 1997, pp. 1377-1380.

Fallone et al., "Noninvasive thermometry with a clinical x-ray CT scanner," Med. Phys., vol. 9, No. 5, 1982, pp. 715-721.

Office Action mailed Nov. 3, 2009 for U.S. Appl. No. 12/401,765.

Notice of Allowance mailed Apr. 15, 2010 for U.S. Appl. No. 12/401,765.

Office Action mailed Apr. 14, 2010 for U.S. Appl. No. 12/402,059.

Office Action mailed Apr. 1, 2010 for U.S. Appl. No. 12/402,141.

Office Action mailed Jun. 16, 2010 for U.S. Appl. No. 12/401,906.

Office Action mailed Jun. 10, 2010 for U.S. Appl. No. 12/401,735.

Office Action mailed Jul. 13, 2010 for U.S. Appl. No. 12/402,225.

Notice of Allowance mailed Aug. 23, 2010 for U.S. Appl. No. 12/401,765.

Notice of Allowance mailed Sep. 17, 2010 for U.S. Appl. No. 12/402,059.

Office Action mailed Sep. 23, 2010 for U.S. Appl. No. 12/401,792.

* cited by examiner

BREAST LOCATING MEANS WITH SAMPLE CONTAINER FOR AN INSTRUMENT FOR EXAMINING A FEMALE BREAST

PRIORITY CLAIM

This application claims priority to pending German Application No. DE 102008042430.7 filed on Sep. 29, 2008.

BACKGROUND OF THE INVENTION

1. Field of the Invention

The invention relates to an X-ray machine for imaging a female breast (mammography).

2. Description of Related Art

Various instruments, such as X-ray machines and CT scanners, are used for examining a female breast. An embodiment of a CT scanner is disclosed, for example, in U.S. Publication No. 2006/0094950. The CT scanner disclosed in the U.S. Publication comprises a rotating gantry, which has an X-ray tube and an X-ray detector, located below a patient table on which a patient to be examined rests. A breast of the patient to be examined projects through an opening in the patient table and into a ray path of the X-ray tube and detector.

BRIEF SUMMARY OF THE INVENTION

The following description of the objective of the disclosure provided herein and the description of embodiments of an X-ray machine and methods for imaging a breast is not to be construed in any way as limiting the subject matter of the appended claims.

An objective of the disclosure provided herein is to provide an X-ray machine and a method for operating an X-ray machine for examining a breast of a female patient with higher speed and resolution, so that a better diagnostic evaluation can be achieved. Another objective of the disclosure is to provide a corresponding means for locating a female breast within the X-ray machine.

BRIEF DESCRIPTION OF THE DRAWINGS

In the following the invention is described by way of example, without limitation of the general inventive concept, on examples of embodiment and with reference to the drawings.

Figure 1:
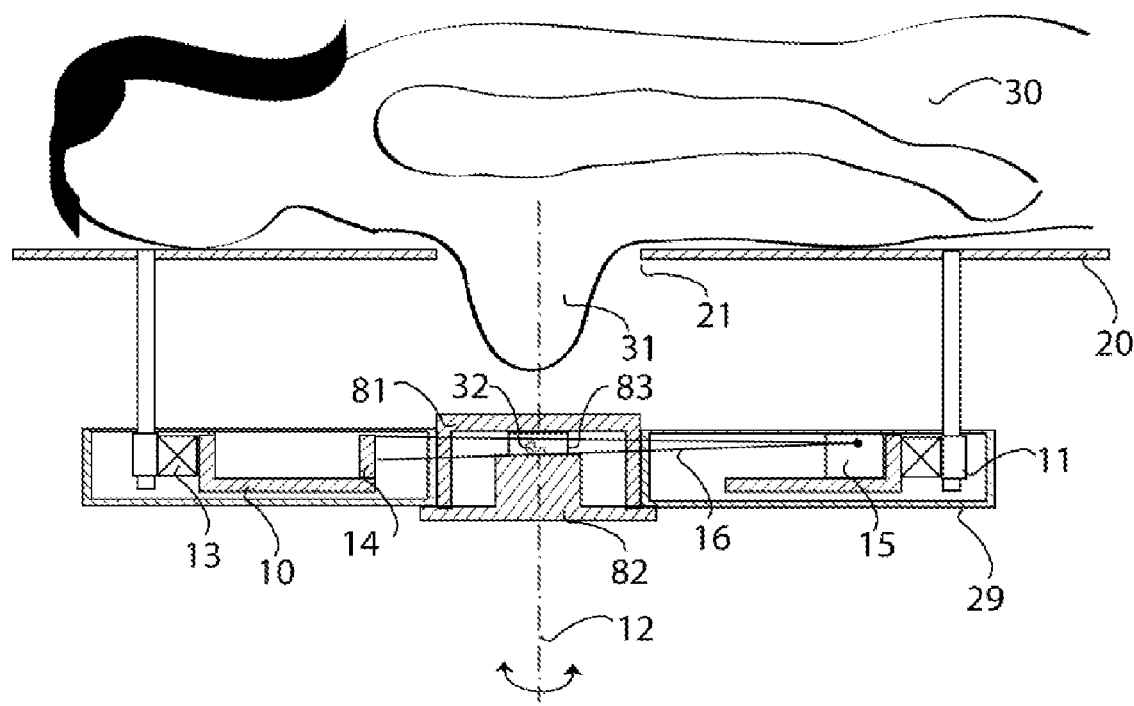
FIG. 1 shows a side view of a cross-section through an embodiment of an X-ray machine that may be used for examining a breast of a patient.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

FIG. 1 shows a side view of a cross-section through an embodiment of an X-ray machine that may be used for examining a breast of a patient. A patient 30 lies on a patient table 20. A gantry 10, which in this embodiment is spiral computer tomography (CT) scanner, is located below the patient. A patient's breast 31 is suspended through a breast cutout portion 21 into an exposure range of the gantry. Within a gantry housing 29, the gantry 10 has an X-ray tube 15 which generates a beam of X-ray radiation 16. The beam of X-ray radiation 16 may be alternatively referred to herein as a beam of rays or a fan beam. Radiation of the fan beam penetrates the breast 31 and is intercepted by a detector 14. In order to image the entire breast, the gantry 10 is rotated by means of a gantry pivot bearing 13 about a rotational axis 12. Simultaneously with the rotation, the gantry 10 is displaced by a gantry lift drive 11 parallel to the rotational axis 12, in this case in a vertical direction, so that the breast is scanned along a spiraling direction.

As shown in FIG. 1, a sample receptacle 83 containing, e.g., a tissue sample 32, is also located within a detecting range of the gantry 10 next to the breast 31. Instead of a tissue sample, the sample receptacle 83 may alternatively contain a material sample or a reference material. The sample receptacle 83 is positioned within the detecting range of the gantry 10 by means of a sample adapter 82. A cover 81 is disposed above the tissue sample 32 and coupled to the sample adapter 82.

FIG. 1 illustrates one embodiment of a position of the gantry 10 in which the tissue sample 32 can be examined. An advantage of such a design is that the tissue sample 32 and the breast 31 of the patient 30 can be examined in the same scanning operation. For example, after examining the tissue sample 32, the gantry 10 can be moved upwards in the direction towards the breast by means of the gantry lift drive 11 to examine the breast 31. Thus, the breast 31 and the tissue sample 32 can be covered with one single scan of the gantry 10.

In the embodiment of FIG. 1, the sample adapter 82 is inserted into the gantry housing 29. However, other embodiments may include alternative means for inserting the sample adapter 82 into the gantry 10. In one embodiment, means for fastening the sample adapter 82 in the gantry may include, for example, screws, magnets, or a quarter-turn fastener. If such means are used, a separate scanning operation may be performed for the contents of the sample receptacle 83.

Figure 2:
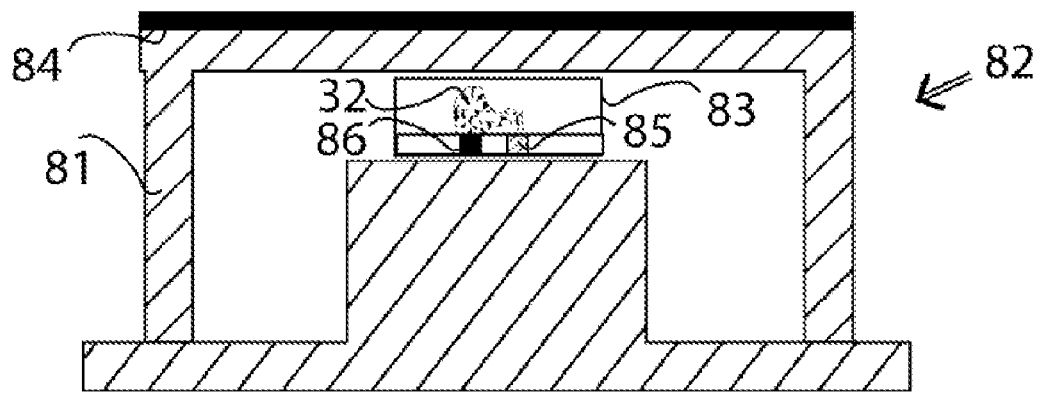
FIG. 2 shows a detailed view of a cross-section through an embodiment of a sample adapter that may be used, in some embodiments, for disposing a tissue sample within an imaging region of an X-ray machine.

FIG. 2 illustrates a detailed cross-section through an embodiment of the sample adapter 82. As shown in FIG. 2, a radiation screen 84 is mounted above the cover 81. The radiation screen 84 prevents the patient from receiving an additional radiation load during irradiation of the sample(s). In addition to tissue sample 32, a first reference material 85 and a second reference material 86 may be disposed within the sample receptacle 83, as shown in FIG. 2.

Figure 3:
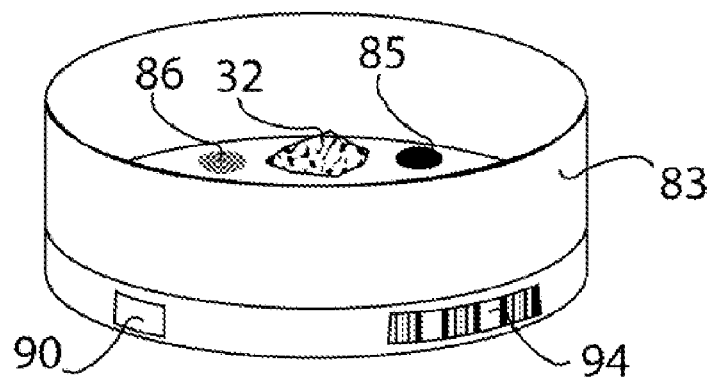
FIG. 3 shows a plan view of an embodiment of a sample receptacle that may be used for housing a tissue sample.

FIG. 3 shows a plan view of an embodiment of a sample receptacle 83. The sample receptacle 83 shown in FIG. 3 comprises a container which, by way of example, contains a tissue sample 32, a first reference material 85, and a second reference material 86. For an unequivocal identification or assignment, an RFID transponder 90 and also a barcode 94 (unit code) are attached to the container portion of the sample receptacle.

Figure 4:
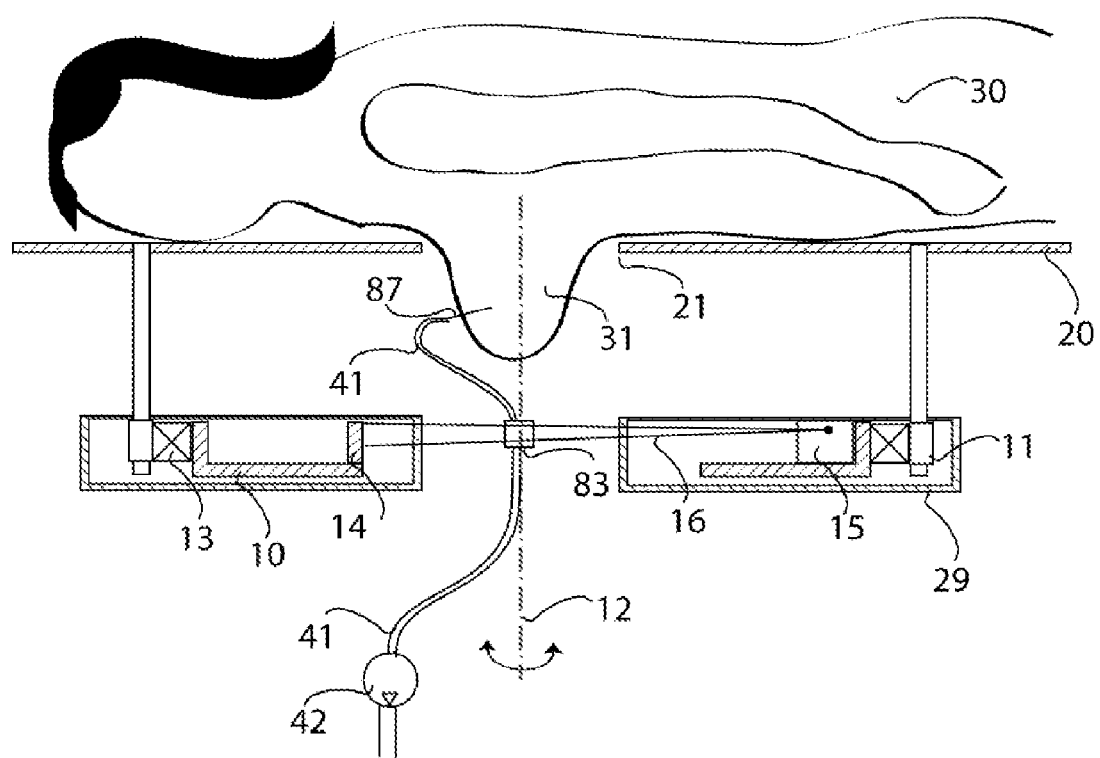
FIG. 4 shows a side view of a cross-section through another embodiment of an X-ray machine for examining a breast of a patient, wherein the X-ray machine comprises a vacuum biopsy device.

FIG. 4 shows a side view of a cross-section through another embodiment of an X-ray machine for examining a breast of a patient. The embodiment shown in FIG. 4 includes many of the components shown in FIG. 1 and described above. Components with like numerals will not be further described herein for the sake of brevity.

In general, the X-ray machine shown in FIG. 4 differs from that shown in FIG. 1 by including a vacuum biopsy facility. Tissue samples can be taken from a breast 31 by means of a vacuum biopsy needle 87. Tubing 41 connects the vacuum biopsy needle 87 to the sample receptacle 83, which in turn is connected via tubing 41 to a vacuum pump 42. Tissue samples cut out of the breast 31 with the vacuum biopsy needle 87 are carried by vacuum pressure into the sample receptacle 83, where they can be examined by means of the gantry 10. Although not shown in FIG. 4, the sample receptacle 83 may be coupled to the gantry 10 by means of the sample adapter 82 shown in FIGS. 1-2, or any other the alternative means discussed above. In addition, the X-ray machines described herein are not necessarily restricted to the inclusion of vacuum biopsy devices as shown and described in reference to FIG. 4. In particular, the X-ray machines described herein may include any type of biopsy device having a biopsy needle.

Figure 5:
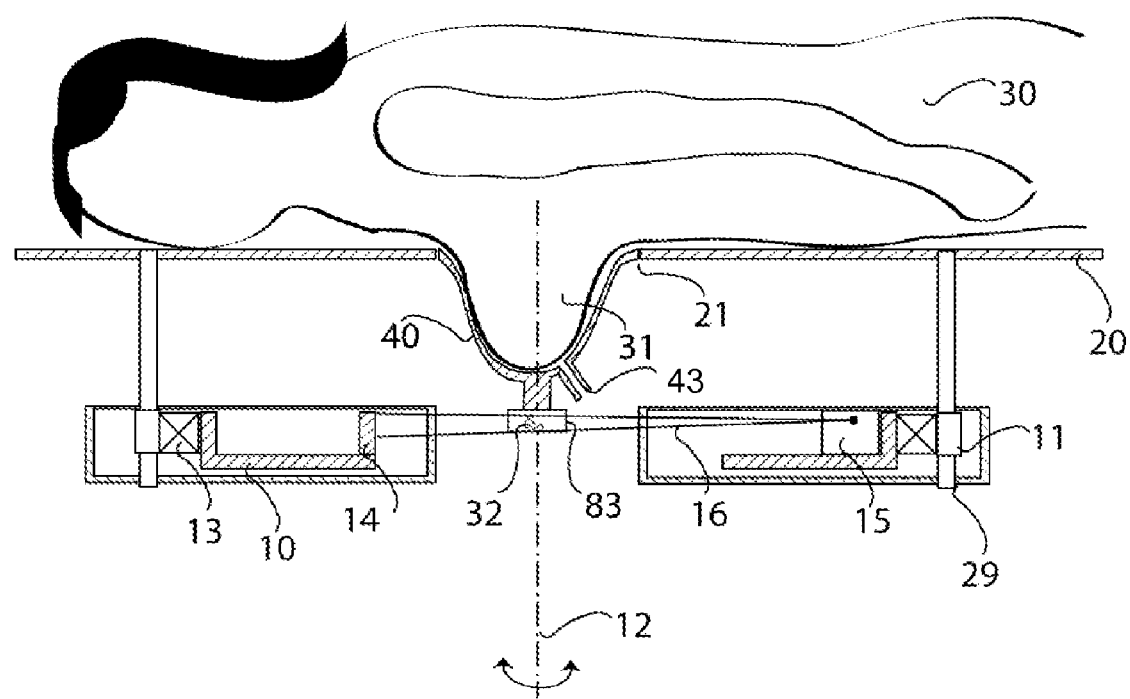
FIG. 5 shows a side view of a cross-section through another embodiment of an X-ray machine for examining a breast of a patient, wherein the X-ray machine comprises a device for locating a breast within an imaging region of the X-ray machine.

FIG. 5 shows a side view of a cross-section through another embodiment of an X-ray machine for examining a breast of a patient. The embodiment shown in FIG. 5 includes many of the components shown in FIGS. 1 and 4 and described above. Components with like numerals will not be further described herein for the sake of brevity.

In general, the X-ray machine shown in FIG. 5 differs from previous embodiments by including a device in the form of a cup 40 for locating a breast within the X-ray machine. In the embodiment of FIG. 5, the locating device is attached to the patient support surface 20 of the X-ray machine. In one embodiment, the cup may have a connection 43 for a vacuum pump (e.g., pump 42 shown in FIG. 4). Unlike the previous embodiments, which dispose a sample container 83 on the gantry 10, the embodiment shown in FIG. 5 disposes a sample container 83 on the cup 40, preferably on the rotational axis 12 of the gantry 10.

An embodiment of an X-ray machine for examining a breast 31 of a female patient 30 comprises a gantry 10, preferably a spiral CT (computer tomograph) gantry. The gantry 10 is rotatable about a rotational axis 12 and is displaceable parallel to the rotation axis simultaneously, or at least in correlation with, the rotational movement. In one embodiment, the displacement is effected simultaneously with the rotational movement, so that a spiral-shaped track about a cylindrical imaging region occurs.

As illustrated in the Figures, the X-ray machine has a supporting surface 20 on which the patient 30 may be positioned, so that the breast 31 to be examined projects into an imaging range of the gantry. The X-ray machine also has a sample receptacle 83, which is also disposed within the imaging range of the gantry 10. The sample receptacle 83 may contain a tissue sample 32 obtained from the patient's breast, as well as possibly other materials. The embodiments of X-ray machines described above enable various tissue samples and/or materials to be examined along with the breast in the same scan operation. For example, a breast of the patient can be surveyed in a first imaging step. In a second imaging step, a tissue sample or a reference material disposed within the sample receptacle 83 can be examined. In some embodiments, the tissue samples and/or materials disposed within the sample receptacle 83 may be examined instead of the patient's breast 31.

In one embodiment, the X-ray machine is preferably set into a high-resolution operating mode to scan the sample(s) disposed within the sample receptacle 83. When scanning the breast, it is typically desired that the entire breast volume be surveyed within a short period of time (e.g., typically 10 seconds), because the patient should not breathe during this entire scanning time. However, since the tissue sample is removed from the patient, a substantially longer period of scanning time is available for scanning the substantially smaller volume of the tissue sample or reference material contained within the sample receptacle. The longer scan time enables scans to be performed using a distinctly smaller focal point of X-ray radiation. Furthermore, it is not necessary to perform a spiral scan on the tissue samples, because of the small size of the tissue samples or reference material. The gantry can, therefore, be moved along a circular track or remain in a fixed position.

In most cases, a substantially higher resolution is achieved when imaging tissue samples as described above than with imaging of a breast. Here it is possible to obtain exact diagnostic information concerning the kind and morphology of the tissue sample or a tumor contained therein. Furthermore, comparisons can be made with high accuracy between the breast tissue and the contents of the sample container. Tolerances which arise due to time-staggered exposures of a breast and a sample in other diagnostic instruments do not occur here. Furthermore, the X-ray machine described herein enables exposures to be made of reference material(s) along with a breast with small time delay. This permits particularly precise calibration of the X-ray machine, thereby providing high quality images yielding better diagnostic information.

In one embodiment, a three-dimensional examination of a tissue sample can be performed with the X-ray machines described above without the patient. In the embodiments described above, no separate instrument is needed for examining the tissue sample.

In one embodiment, a tissue sample that has just been taken from a patient positioned on a support surface 20 of the X-ray machines described herein can be examined by X-ray technology. In other words, it is often not necessary for the patient to leave the support surface 20.

In one embodiment, the gantry 10 is configured so that a sample adapter 82 for accommodating the sample container 83 can be inserted into the gantry without the need for a separate holder. In another embodiment, the sample adapter 82 may be inserted into a holder 29 in the gantry. In one embodiment, the sample adapter may be inserted into the gantry itself or the holder prior to an examination.

In one embodiment, a biopsy device may be included within the X-ray machine. In some cases, the biopsy device may be a vacuum biopsy device, but the X-ray machines described herein are not necessarily so limited. In any case, tissue can be taken from a breast by means of a biopsy needle. The tissue sample is transported into a sample receptacle, where it can be imaged by the gantry.

In some embodiments, the biopsy device may be a sub-pressure biopsy device. Thus, tissue can be taken from a breast by means of a sub-pressure biopsy needle. The tissue sample is transported by means of sub-pressure into a sample receptacle, where it can be imaged by the gantry.

In one embodiment, the sample adapter 82 is provided with a radiation screen 84, so that during imaging of the contents of the sample receptacle 83, the radiation load on the patient located closely above the receptacle is minimal.

In one embodiment, the sample adapter 82 and/or the sample receptacle 83 is provided with at least one automatic identification system. Examples of such an identification system include, but are not limited to, an RFID transponder 90, a barcode 94, an RFID transponder 90 and at least one barcode 94, and other means for identification.

A sample adapter 82 for insertion into an X-ray machine is also disclosed herein. As noted above, the sample adapter is configured for supporting and housing a sample receptacle 83. In one embodiment, the sample adapter 82 and/or the sample receptacle 83 may be provided with at least one automatic identification system. Examples of such an identification system include, but are not limited to, an RFID transponder, a barcode 94, an RFID transponder 90 and at least one barcode 94, and other means for identification.

A device for locating a breast 31 of a female patient 30 in an X-ray machine is also disclosed herein. As noted above, the device for locating the breast comprises a sample receptacle 83 and/or a sample adapter 82 into which a tissue sample 32 and/or a reference material 85 can be introduced. In one embodiment, the tissue sample and/or reference material can be scanned and imaged together with the patient's breast in one scanning operation. In one embodiment, the locating device and/or the sample adapter 82 and/or the sample receptacle 83 may be provided with at least one automatic identification system. Examples of such an identification system include, but are not limited to, an RFID transponder, a barcode 94, an RFID transponder 90 and at least one barcode 94, and other means for identification.

A method for examining a breast of a female patient is also disclosed herein. An embodiment of the method is performed with a spiral CT scanner. This scanner has a gantry 10 which is rotatable about the breast and simultaneously, or in correlation with the rotation, displaceable along a distance parallel to a wall of the breast. Scanning of the breast is, thereby, effected along a spiral-shaped curve around the breast.

In one embodiment, the method comprises: (1) positioning a patient 30 on a support surface 20 of an X-ray machine so that a breast to be examined projects into an imaging space of the X-ray machine; (2) obtaining an X-ray image of the breast with the gantry 10; (3) removing a tissue sample from the breast at a position determined from the X-ray image; and (4) obtaining an X-ray image of the tissue sample with the gantry, preferably in a high-resolution mode.

In one embodiment, steps 1 and 3 may be modified or omitted to provide an alternative X-ray method. The method set forth above is independent of the position of the patient 30 or the orientation of the support surface 20. Thus, the method described herein may be used with X-ray machines in which the patient lies on a horizontal patient table, or with vertically disposed X-ray machines requiring a patient to stand in front of the X-ray machine. Of course, it can be applied also to X-ray machines, in which the patient table or support surface is disposed at any desired inclination.

It will be appreciated to those skilled in the art having the benefit of this disclosure that this disclosure is believed to provide X-ray machines and methods for imaging a breast. Sample adapters and devices for locating a breast within an X-ray machine are also disclosed herein. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. An X-ray machine for imaging a breast of a female patient, comprising:
   a gantry that is rotatable about a rotational axis and simultaneously movable in a direction parallel to the rotational axis, and thus, covers a cylindrical imaging region;
   a support surface for positioning the patient so that the breast to be imaged projects into the imaging region of the gantry;
   a sample receptacle disposed within the imaging region of the gantry, wherein the sample receptacle is adapted for housing at least one of a tissue sample and a reference sample; and
   wherein a range of movement of the gantry is dimensioned for imaging at least one of the breast and a content of the sample receptacle.

2. The X-ray machine according to claim 1, wherein the gantry comprises a plurality of operating modes, wherein an operating mode with a smaller focal point is selected to image at least one of a tissue sample and a reference material, and wherein an operating mode with a larger focal point is selected to image the breast.

3. The X-ray machine according to claim 1, further comprising a sample adapter for accommodating the sample receptacle, wherein the sample adapter is adapted to be inserted into the gantry.

4. The X-ray machine according to claim 3, wherein the sample adapter comprises a radiation screen for reducing a radiation load on the patient during scanning of the contents of the sample receptacle.

5. The X-ray machine according to claim 3, wherein the sample adapter comprises at least one of an RFID transponder, a barcode, and further identification means for identifying at least one of the sample adapter and the contents contained within the sample receptacle.

6. The X-ray machine according to claim 1, further comprising a cup for locating the breast within the imaging region of the gantry, wherein the sample receptacle is attached to the cup.

7. The X-ray machine according to claim 1, further comprising a biopsy device comprising a biopsy needle.

8. The X-ray machine according to claim 7, wherein the biopsy device is a vacuum biopsy device comprising a vacuum biopsy needle connected to a vacuum pump via tubing, wherein a tissue sample taken from the patient's breast with the vacuum biopsy needle is conveyed with the aid of vacuum into the sample receptacle.

9. A method for examining a breast of a female patient using a gantry having a spiral CT scanner comprises:
   positioning the patient on a support surface so that a breast to be examined projects into an imaging region of the gantry;
   obtaining an X-ray image of the breast with the gantry;
   removing a tissue sample from the breast at a location determined by the X-ray image; and
   obtaining an X-ray image of the tissue sample with the gantry.

10. The method according to claim 9, wherein the step of obtaining an X-ray image of the tissue sample is performed at higher resolution than the step of obtaining an X-ray image of the breast.

11. The method according to claim 9, wherein the step of removing a tissue sample is performed with the aid of a vacuum pressure biopsy needle.

* * * * *